US010888651B2

(12) United States Patent
Dedig et al.

(10) Patent No.: US 10,888,651 B2
(45) Date of Patent: Jan. 12, 2021

(54) MAGNETIC PRESSURE JACKET FOR FLUID INJECTOR

(71) Applicant: BAYER HEALTHCARE LLC, Whippany, NJ (US)

(72) Inventors: James Dedig, Pittsburgh, PA (US); Ralph Schriver, Tarentum, PA (US); Patrick Campbell, Pittsburgh, PA (US); Herbert Grubic, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 151 days.

(21) Appl. No.: 16/160,389

(22) Filed: Oct. 15, 2018

(65) Prior Publication Data

US 2019/0046719 A1  Feb. 14, 2019

Related U.S. Application Data

(63) Continuation of application No. 15/028,784, filed as application No. PCT/US2014/061144 on Oct. 17, 2014, now Pat. No. 10,124,110.
(Continued)

(51) Int. Cl.
*A61M 5/00* (2006.01)
*A61M 5/145* (2006.01)
*A61M 5/20* (2006.01)

(52) U.S. Cl.
CPC ........ *A61M 5/007* (2013.01); *A61M 5/14546* (2013.01); *A61M 5/14566* (2013.01);
(Continued)

(58) Field of Classification Search
CPC ........ A61M 2005/14553; A61M 2005/14573; A61M 2209/082; A61M 5/007; A61M 5/14546; A61M 5/14566
See application file for complete search history.

(56) References Cited

U.S. PATENT DOCUMENTS 7,549,977 B2  6/2009  Schriver et al.
7,553,294 B2  6/2009  Lazzaro et al.
(Continued)

FOREIGN PATENT DOCUMENTS

JP    3112088 U      8/2005
WO    2006044409 A2  4/2006
WO    2012155035 A1  11/2012

OTHER PUBLICATIONS

International Preliminary Report with Written Opinion dated Apr. 28, 2016 from PCT/US2014/061144.
(Continued)

*Primary Examiner* — Rebecca E Eisenberg
(74) *Attorney, Agent, or Firm* — David Schramm; Joseph L. Kent; James R. Stevenson

(57) ABSTRACT

A fluid injector having at least one injector head with a front end configured to releasably receive the at least one syringe is described. The fluid injector further includes at least one pressure jacket releasably associated with the front end of the at least one injector head for securing the at least one syringe during an injection procedure. A connection mechanism releasably connects the at least one pressure jacket to the front end of the at least one injector head. The connection mechanism includes at least one electromagnet.

15 Claims, 11 Drawing Sheets

Related U.S. Application Data

(60) Provisional application No. 61/892,820, filed on Oct. 18, 2013.

(52) U.S. Cl.
CPC ..... *A61M 5/20* (2013.01); *A61M 2005/14553* (2013.01); *A61M 2005/14573* (2013.01); *A61M 2209/082* (2013.01)

(56) References Cited

U.S. PATENT DOCUMENTS

| | | |
|---|---|---|
| 2007/0106153 A1 | 5/2007 | Neer et al. |
| 2010/0137832 A1 | 6/2010 | Mathews et al. |
| 2015/0057614 A1 | 2/2015 | Curtis |
| 2015/0231325 A1* | 8/2015 | Neer .................... A61M 5/007 600/432 |

OTHER PUBLICATIONS

International Search Report and Written Opinion dated Mar. 4, 2016 from PCT/US2015/057751.
"Supplementary European Search Report from EP Application No. 14853894", dated Jun. 29, 2017.
International Search Report dated Feb. 6, 2015 from PCT/US2014/061144.

\* cited by examiner

MAGNETIC PRESSURE JACKET FOR FLUID INJECTOR

CROSS-REFERENCE TO RELATED APPLICATIONS

This application is a continuation of U.S. Ser. No. 15/028,784, filed Apr. 12, 2016, which is a U.S. national stage filing under 35 U.S.C. § 371 of International Application No. PCT/US2014/061144, filed Oct. 17, 2014, which claims priority to U.S. Provisional Application No. 61/892,820, entitled "Magnetic Pressure Jacket for Dual Head Injector" and filed on Oct. 18, 2013. The disclosure of each of these applications is incorporated by reference herein in its entirety.

BACKGROUND OF THE DISCLOSURE

Field of the Disclosure

The present disclosure is directed to medical fluid delivery applications and, particularly, to a magnetically-retained pressure jacket configured for use with a fluid injector.

Description of Related Art

In the medical field, patients often are injected with one or more medical fluids in various procedures. In such procedures, which require a controlled injection of a volume of one or more fluids into a patient, a needle is used as a conduit for the fluid and is connected to a syringe by a connector tube. One or more syringes may be mounted on a motorized fluid injector having one or more injector heads. In some embodiments, the fluid injector may have two injector heads capable of delivering distinct medical fluids from two separate syringes.

For long term compatibility with injectable fluids, syringes for use with the fluid injector may be made of polypropylene with a certain minimum wall thickness. Syringe thickness is an important design factor, as typical pressures of up to 1200 psi are used to inject the fluid into a patient. Pressure jackets are known in the art for enclosing and retaining syringes while in use. A pressure jacket serves to limit radial expansion of the syringe barrel due to fluid pressure during an injection procedure. Excessive radial expansion of the syringe may lead to bursting or to leaks of the pressurized fluid around the seals of the syringe plunger. During an injection procedure, an exterior wall of the syringe expands against an interior wall of the pressure jacket due to the extreme forces that act on the syringe in a radially outward direction. Additionally, the syringe and/or the pressure jacket may experience significant axial movement during a high pressure injection due to the elastic nature of the structural components restraining the syringe. For example, a force of 2400 pounds may be required to restrain the forward motion of a single 150 ml syringe with a cross-section of 1.6 in$^2$ at 1200 psi. Such a force may result in as much as 0.100 inches of axial movement of the syringe and pressure jacket during the injection.

Certain present pressure jackets have a one-piece design, where the syringe is inserted into the pressure jacket from the front (distal) end of the pressure jacket. In these embodiments, the neck of the syringe protrudes from the front end of the pressure jacket such that the syringe may be connected to fluid lines leading to the patient. These pressure jackets are typically retained on the injector head by a coupling member that engages a groove circumscribing a proximal (rear) end of the pressure jacket.

However, such an arrangement is associated with a number of disadvantages. Fluid spilled during loading of the syringe and purging of air from the syringe may get inside the pressure jacket and the circumferential groove, thereby complicating the cleaning procedure. Because the pressure jacket is retained at the proximal (rear) end, it is subjected to high axial stress in the region of the circumferential groove during an injection procedure. Such axial stress can sometimes lead to slipping of the pressure jacket during the injection procedure, which may result in a loud and unsettling noise. In addition, continuous installation and removal of the pressure jacket from the injector head can cause significant wear on the circumferential groove.

SUMMARY OF THE DISCLOSURE

While various fluid injectors are known in the medical field, improved fluid injectors are continually desired. In view of certain disadvantages of the existing fluid injectors having at least one pressure jacket, there is a need in the art for an improved fluid injector with a pressure jacket that simplifies loading and unloading of the syringe. An additional need exists for a pressure jacket mounting interface that permits a relative motion between the injector head and the pressure jacket during an injection procedure. An additional need exists for a portable fluid delivery system having one or more of the above-noted advantages.

In certain embodiments, a fluid injector for use with at least one syringe is provided. The fluid injector may include at least one injector head having a front end configured to releasably receive the at least one syringe. The injector may further include at least one pressure jacket releasably associated with the front end of the at least one injector head for securing the at least one syringe during an injection procedure. A connection mechanism may be provided for releasably connecting the at least one pressure jacket to the front end of the at least one injector head. The connection mechanism may include at least one magnet.

In other embodiments, the connection mechanism may include a first magnet on the at least one pressure jacket and a second magnet on the at least one injector head. Alternatively, the at least one magnet may be formed on one of the at least one pressure jacket and the at least one injector head, while the other of the at least one pressure jacket and the at least one injector head may include a ferromagnetic material. For example, in one embodiment the at least one injector head may include the at least one magnet and the at least one pressure jacket may include a ferromagnetic material configured for magnetically interacting with the at least one magnet. The ferromagnetic material may be formed on a terminal surface of the at least one pressure jacket that engages the at least one injector head. The at least one magnet may be a plurality of magnets arranged in a shape corresponding to the terminal surface of the at least one pressure jacket. The at least one magnet may be received within a pocket formed on the front end of the at least one injector head. In another embodiment, the at least one magnet may be on the pressure jacket and the at least one injector head may include a ferromagnetic material configured for magnetically interacting with the at least one magnet.

In other embodiments, at least one arm may be pivotally connected at a proximal end to the at least one injector head for retaining a distal end of the at least one pressure jacket and to engage the distal end of the at least one syringe. The at least one arm may be pivotable between a first position and a second position. The at least one arm may be magnetically retained in the first position, for example, in the engaged position. A holding bracket may be pivotally connected to a distal end of the at least one arm for engaging a distal end of the at least one pressure jacket and a distal end of the at least one syringe. The holding bracket may be pivotable between a first position and a second position. The holding bracket may include at least one magnet and may be magnetically retained in the first position, for example, in the engaged position. In each embodiment, the at least one magnet in the injector head, the proximal end of the pressure jacket, the distal end of the pressure jacket, the at least one arm, and/or the holding bracket, may be a permanent magnet, for example, a ferromagnet, a rare earth magnet, or an alnico magnet, or an electromagnet.

In other embodiments, a pressure jacket for use with a fluid injector is provided. The pressure jacket may include a tubular body having a proximal end and a distal end, a syringe receiving opening at the distal end configured for receiving a syringe within an interior of the tubular body, and a connection portion with a terminal surface at the proximal end configured for releasably connecting the pressure jacket to the fluid injector. The pressure jacket may have at least one connection element on at least a portion of the connection portion. The at least one connection element may be configured to magnetically interact with the fluid injector for releasably connecting the pressure jacket to the fluid injector. The at least one connection element may be a ferromagnetic element or a magnet. The at least one connection element may be ring-shaped.

In some embodiments, a fluid injector for use with at least one syringe is provided. The fluid injector may include at least one injector head having a front end configured to releasably receive the at least one syringe. The injector may further include at least one pressure jacket releasably associated with the front end of the at least one injector head for securing the at least one syringe therein during an injection procedure. At least one arm may be pivotally connected at a proximal end to the at least one injector head for retaining a distal end of the at least one pressure jacket. The at least one arm may be pivotable between a first position and a second position. At least one connection mechanism may be configured for at least one of (A) releasably connecting the proximal end of the at least one pressure jacket to the front end of the at least one injector head, and (B) retaining the at least one arm in the first position. The connection mechanism may include at least one magnet. A holding bracket may be pivotally connected to a distal end of the at least one arm for engaging a distal end of the at least one pressure jacket and a distal end of the at least one syringe. The holding bracket may be pivotable between a first position and a second position. The holding bracket may be magnetically retained in the first position, such as a position engaging the distal end of the at least one pressure jacket and the distal end of the at least one syringe.

These and other features and characteristics of the fluid injector and the pressure jacket configured for releasable connection with the fluid injector, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claims, the singular form of "a", "an", and "the" include plural referents unless the context clearly dictates otherwise.

DETAILED DESCRIPTION

Figure 1:
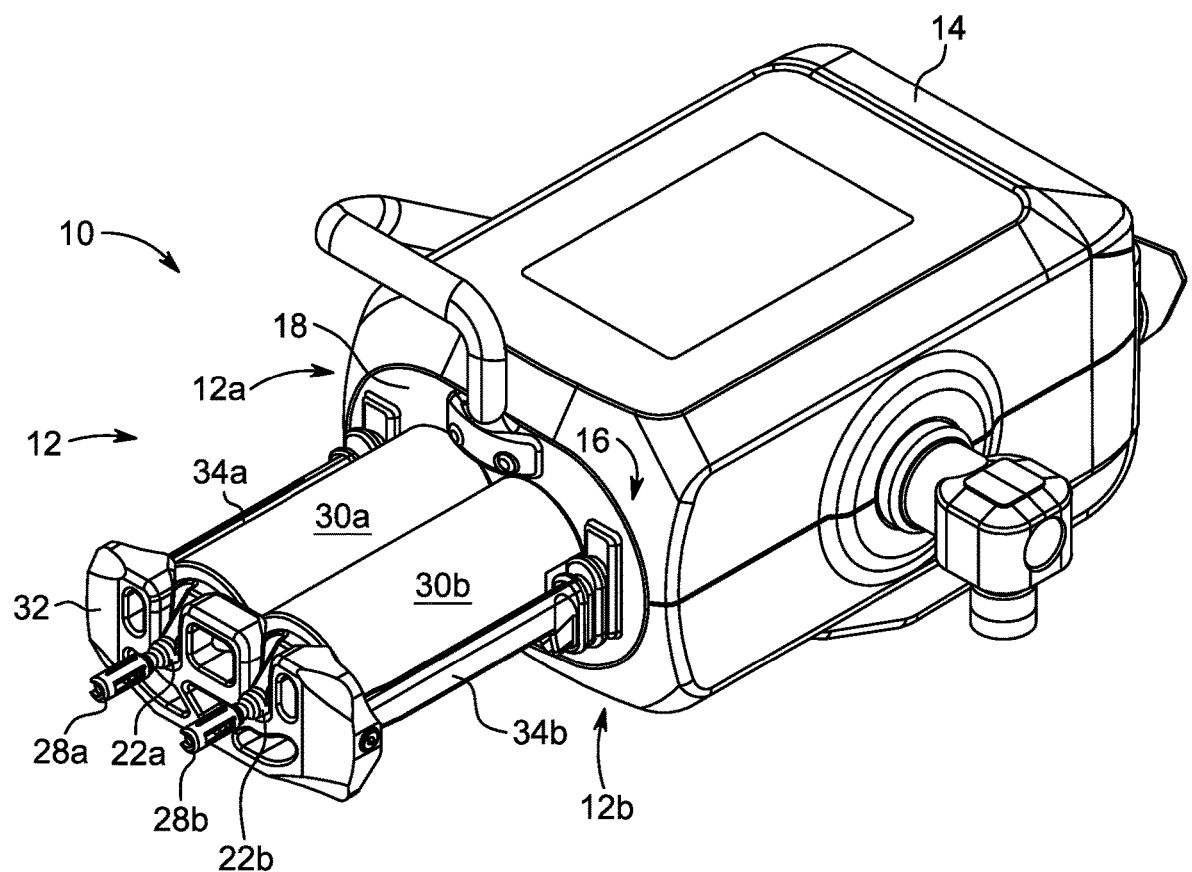
FIG. 1 is a perspective view of a fluid injector in accordance with one embodiment.

For purposes of the description hereinafter, spatial orientation terms shall relate to the referenced embodiments as they are oriented in the drawing figures. For example, the terms "upper", "lower", "right", "left", "vertical", "horizontal", "top", "bottom", "lateral", "longitudinal", and derivatives thereof shall relate to the embodiments as they are oriented in the drawing figures. When used in relation to the syringe and/or the pressure jacket, the term "proximal" refers to the portion of the syringe and/or the pressure jacket nearest the fluid injector when the syringe and/or pressure jacket is oriented for connecting to the fluid injector. The term "distal" refers to the portion of the syringe and/or pressure jacket farthest away from the fluid injector when the syringe and/or pressure jacket is oriented for connecting to the fluid injector. It is to be understood, however, that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

Referring to the drawings in which like reference characters refer to like parts throughout the several views thereof, the present disclosure is generally directed to front loadable pressure jacket systems for use with a fluid injector having an injector head with a housing and a front end.

With reference to FIG. 1, a fluid injector 10 includes at least one injector head 12 and an injector housing 14. The injector head 12 may be supported on a support structure (not shown). In some embodiments, such as shown in FIG. 1, the fluid injector 10 may include two injector heads 12a, 12b arranged in a side-by-side orientation. Each injector head 12a, 12b may be formed at a front end 16 of the injector housing 14 and may be configured for receiving and retaining at least one syringe 22a, 22b therein. A faceplate 18 may be attached to the front end 16 of the injector housing 14 and enclose at least a portion of the front end 16 of the injector housing 14. The faceplate 18 may be secured to the front end 16 of the injector housing 14 by conventional means (i.e., mechanical fasteners and the like) or may be integrally formed with the injector housing 14. While FIG. 1 illustrates the fluid injector 10 with two injector heads 12a, 12b, other embodiments of the fluid injector 10 may include a single injector head or more than two injector heads. One embodiment of a dual-head fluid injector is disclosed in U.S. Pat. No. 7,549,977, assigned to the assignee of the present application, which is incorporated herein by reference in its entirety.

Figure 7:
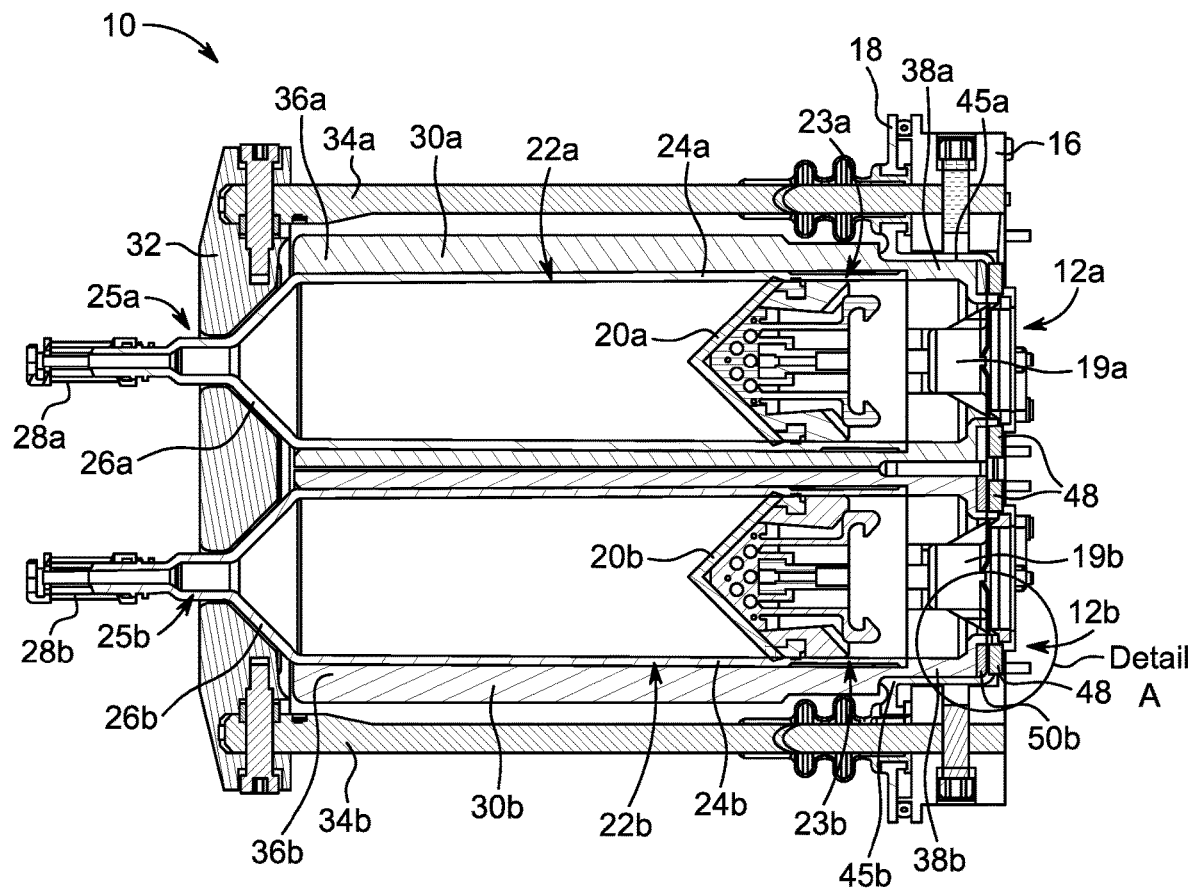
FIG. 7 is a cross-sectional view of the pair of pressure jackets shown in a first, closed position.
Figure 8:
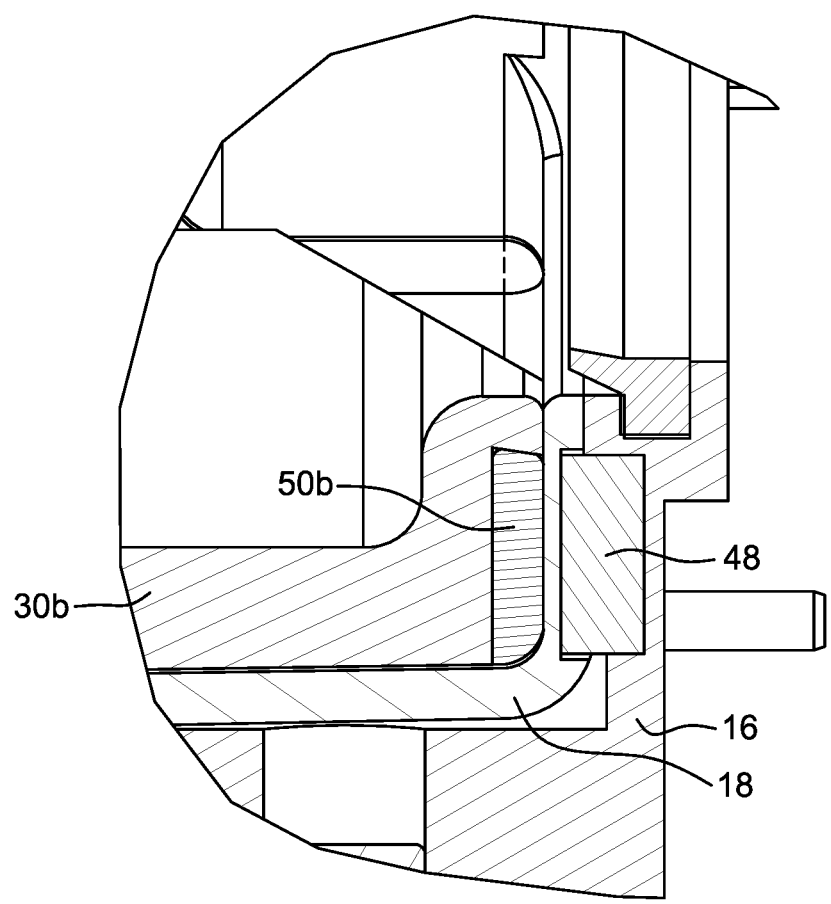
FIG. 8 is an enlarged view of Detail A shown in FIG. 7.

With reference to FIG. 7, each injector head 12a, 12b includes a drive means 19a, 19b, such as a reciprocally driven piston moved by a motor (not shown) which is operated by a controller (not shown). Each drive means 19a, 19b may be configured to extend into and from the respective injector head 12a, 12b through an opening in the front end 16 of the injector housing 14. The drive means 19a, 19b, through the reciprocal movement of the piston, imparts a motive force to plungers 20a, 20b slidably disposed within syringes 22a, 22b, respectively. The plungers 20a, 20b are reciprocally movable within the syringes 22a, 22b.

Each syringe 22a, 22b includes a tubular body 24a, 24b and the plunger 20a, 20b slidably positioned therein, for example, at a proximal or rear end 23a, 23b of the syringe 22a, 22b. The tubular body 24a, 24b includes a neck 25a, 25b having a connector 28a, 28b, such as a luer connector, provided at a distal or front end 26a, 26b of the syringe 22a, 22b, respectively. Each syringe 22a, 22b may be manufactured from metal, glass, plastic, or other conventional material. In some embodiments, the at least one syringe 22a, 22b is made from a clear medical-grade plastic material. At least one fluid path set (not shown) may be coupled to each connector 28a, 28b to deliver fluid from the syringes 22a, 22b to the patient. Syringes 22a, 22b desirably contain a first fluid and a second fluid, respectively. In some embodiments, the first fluid may be a contrast solution for a medical imaging procedure, while the second fluid may be a flushing solution, such as a saline solution. In other embodiments, the first fluid contained within the first syringe 22a may be the same as or different from the second fluid contained within the second syringe 22b.

Figure 2:
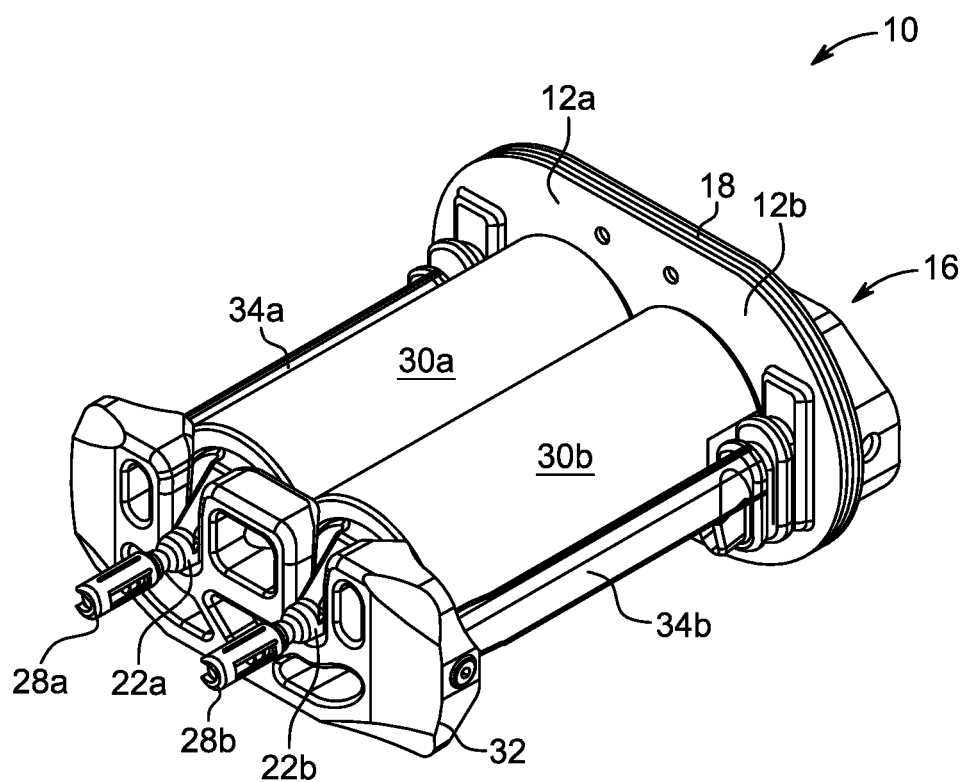
FIG. 2 is a perspective view of a pair of pressure jackets for use with the fluid injector of FIG. 1 with retaining arms shown in a first, closed position.
Figure 4:
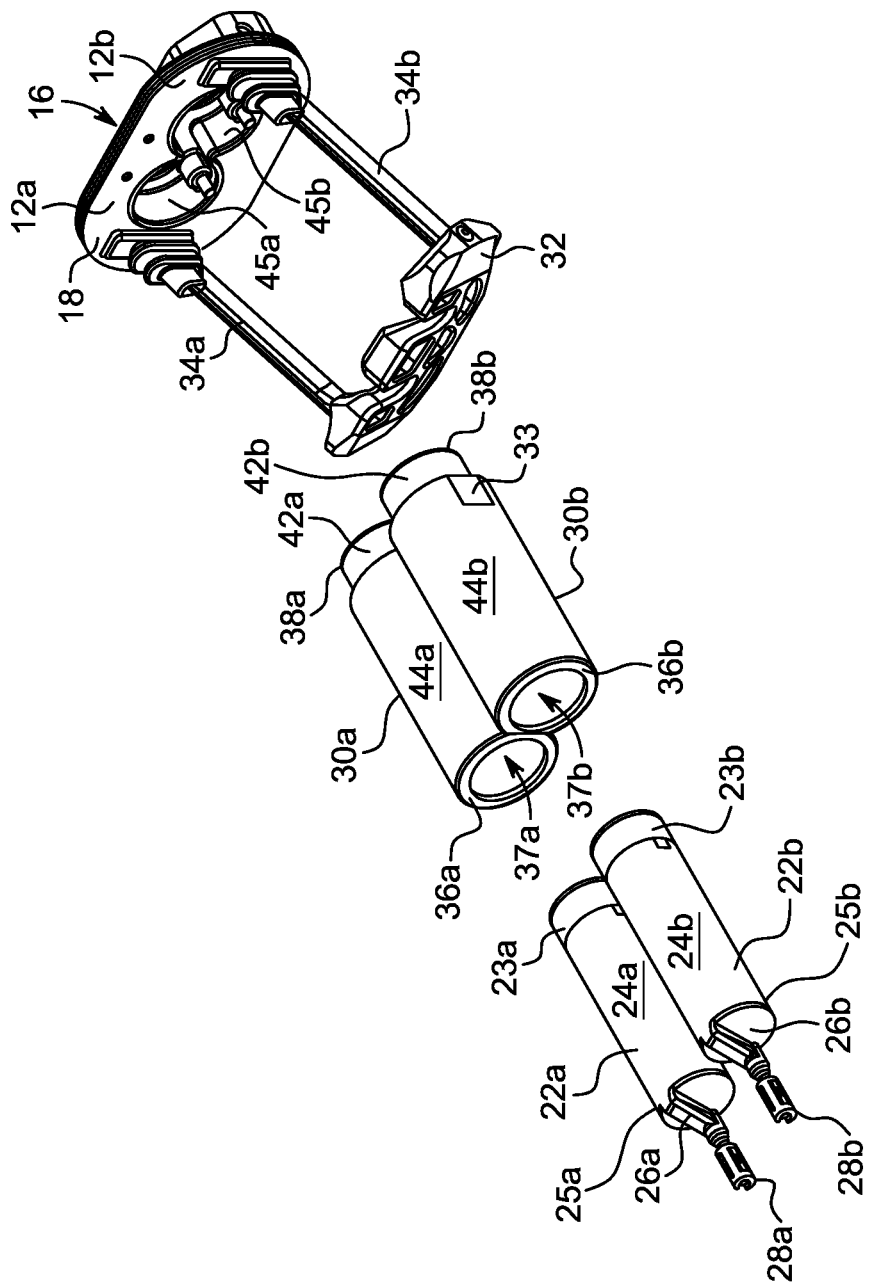
FIG. 4 is an exploded perspective view of FIG. 3.

With continuing reference to FIG. 7, a pressure jacket 30a, 30b is associated with each injector head 12a, 12b. Each pressure jacket 30a, 30b retains the corresponding syringe 22a, 22b radially therein when the syringe 22a, 22b is loaded within the pressure jacket 30a, 30b. Each pressure jacket 30a, 30b supports the respective syringe 22a, 22b and mounts the syringe 22a, 22b to the injector head 12a, 12b, thereby allowing connection of each of the plungers 20a, 20b with the respective drive means 19a, 19b. With reference to FIG. 4, the at least one pressure jacket 30a, 30b may have a generally cylindrical shape with a front or distal end 36a, 36b configured to engage a holding bracket 32 when the holding bracket 32 is in a first, closed position (as shown in FIG. 2). The distal end 36a, 36b of the at least one pressure jacket 30a, 30b may define a syringe receiving mouth or opening 37a, 37b for receiving the syringe 22a, 22b into the pressure jacket 30a, 30b. The at least one pressure jacket 30a, 30b further includes a rear or proximal end 38a, 38b configured to engage a recess 45a, 45b in the faceplate 18 of the injector 10. The proximal end 38a, 38b may have an undercut portion 42a, 42b configured for being received within the recess 45a, 45b, respectively. In other embodiments (not shown), the proximal end 38a, 38b of the at least one pressure jacket 30a, 30b may define a syringe receiving mouth or opening for receiving the syringe 22a, 22b.

In certain embodiments, the at least one pressure jacket 30a, 30b may have a substantially tubular body 44a, 44b that may be manufactured from a translucent or transparent material so that the position of the plungers 20a, 20b within the syringes 22a, 22b may be observed. In some embodiments, a viewing window (shown as 33 in FIG. 4) may be provided on the at least one pressure jacket 30a, 30b. In some embodiments, the at least one pressure jacket 30a, 30b may be made from a medical grade material, such as medical grade plastic, metal, or glass, having sufficient radial strength to retain any radial expansion of the at least one syringe 22a, 22b during an injection procedure. Each tubular body 44a, 44b has an interior surface which conforms to the exterior surface of the body 24a, 24b of the syringe 22a, 22b. The exterior surface of the pressure jackets 30a, 30b may have a flattened portion 35 (shown in FIG. 6) such that the at least one pressure jacket 30a, 30b may be arranged closer together when attached to the injector. The at least one pressure jacket 30a, 30b has an inner diameter sized to smoothly and snugly receive the outer diameter of the syringe 22a, 22b. A typical clearance between the outer diameter of the syringe 22a, 22b and the inner diameter of the pressure jacket 30a, 30b may be about 0.005 inch, although other clearance distances may be considered. Each pressure jacket 30a, 30b may be made from a material capable of restraining the outward radial expansion of the syringe 22a, 22b and syringe body 24a, 24b during an injection procedure. As discussed previously, the syringe 22a, 22b and/or syringe body 24a, 24b itself is typically not capable of withstanding the high pressures associated with certain fluid injection procedures, such as angiography. The pressure jacket 30a, 30b is used to limit the radial expansion of the syringe 22a, 22b and syringe body 24a, 24b, as discussed previously.

Figure 3:
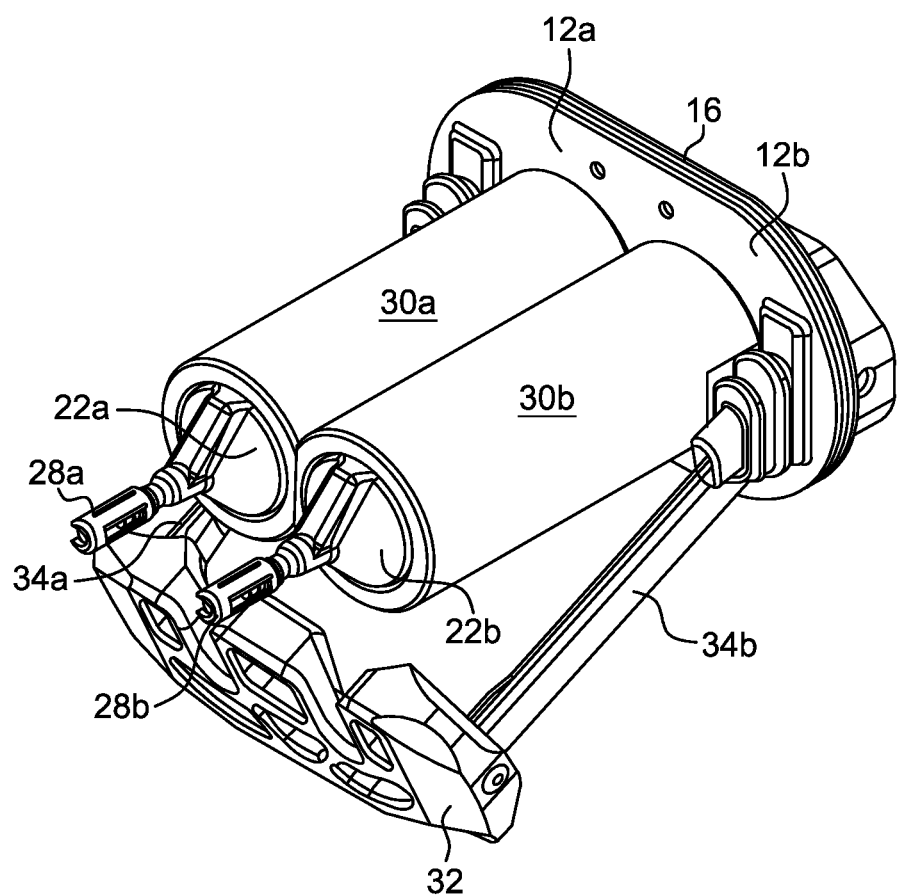
FIG. 3 is a perspective view of the pair of pressure jackets for use with the fluid delivery system of FIG. 1 with the retaining arms shown in a second, open position.
Figure 9:
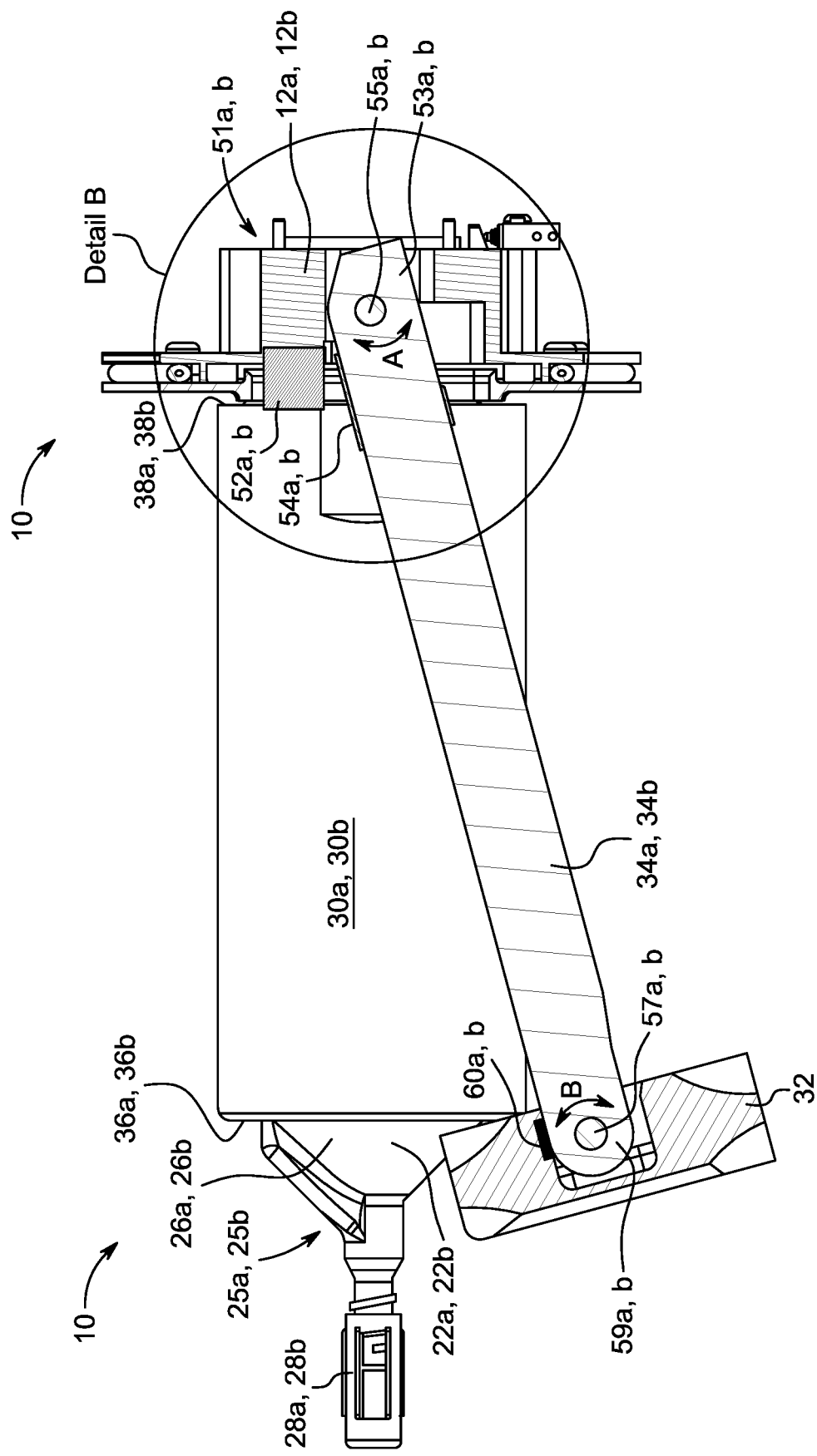
FIG. 9 is a side cross-sectional view of a fluid injector in a second, open position.

In operation, the proximal end 38a, 38b of the at least one pressure jacket 30a, 30b is inserted into the recess 45a, 45b, respectively, on the faceplate 18. The proximal end 23a, 23b of the at least one syringe 22a, 22b may then be inserted into the syringe receiving opening 37a, 37b (shown in FIG. 4) of the at least one pressure jacket 30a, 30b. The tubular body 24a, 24b of the at least one syringe 22a, 22b is retained radially within the corresponding tubular body 44a, 44b of the at least one pressure jacket 30a, 30b. The distal end 26a, 26b of each syringe 22a, 22b and the distal end 36a, 36b of each pressure jacket 30a, 30b are retained by a holding bracket 32 that protrudes at the end of a pair of arms 34a, 34b from the front end 16 of the injector housing 14. The pair of arms 34a, 34b of the holding bracket 32 are pivotable relative to the front end 16 between a first, closed position (FIG. 2) and a second, open position (FIG. 3). With reference to FIG. 9, the arms 34a, 34b pivot about their proximal end 53a, 53b about a pivot point 55a, 55b on the injector 10 in a direction of arrow A. In the closed position (see FIG. 2), the holding bracket 32 engages the distal end 26a, 26b of the syringe 22a, 22b and/or the distal end 36a, 36b of the at least one pressure jacket 30a, 30b to retain the syringe 22a, 22b and the pressure jacket 30a, 30b longitudinally and prevent or restrain movement of the syringes 22a, 22b during an injection procedure. In an open position (see FIG. 2 or 9), the holding bracket 32 pivots downwardly (or upwardly in another embodiment) away from engaging the distal end 26a, 26b of the syringe 22a, 22b and/or the distal end 36a, 36b of the at least one pressure jacket 30a, 30b through a pivoting movement of the arms 34a, 34b to allow the syringe 22a, 22b and/or the pressure jacket 30a, 30b to be inserted/removed from the injector housing 14. The holding bracket 32 may be pivotable about a second pivot 57a, 57b on the distal end 59a, 59b of the arms 34a, 34b. When the holding bracket 32 is in the closed position (FIG. 2), the drive means 19a, 19b can be actuated to selectively drive one or both of the plungers 20a, 20b to expel fluid from or draw fluid into the syringes 22a, 22b, respectively. With reference to FIG. 7, when the motorized piston of the drive means 19a, 19b engages the syringe plunger 20a, 20b, the piston pushes the plunger 20a, 20b forward through the body 24a, 24b of the syringe 22a, 22b toward the distal end 26a, 26b to force fluid out of the syringe neck 25a, 25b. Alternatively, the piston may pull the plunger 20a, 20b rearward through the body 24a, 24b of the syringe 22a, 22b toward the proximal end 23a, 23b to draw fluid into the syringe 22a, 22b.

Figure 5:
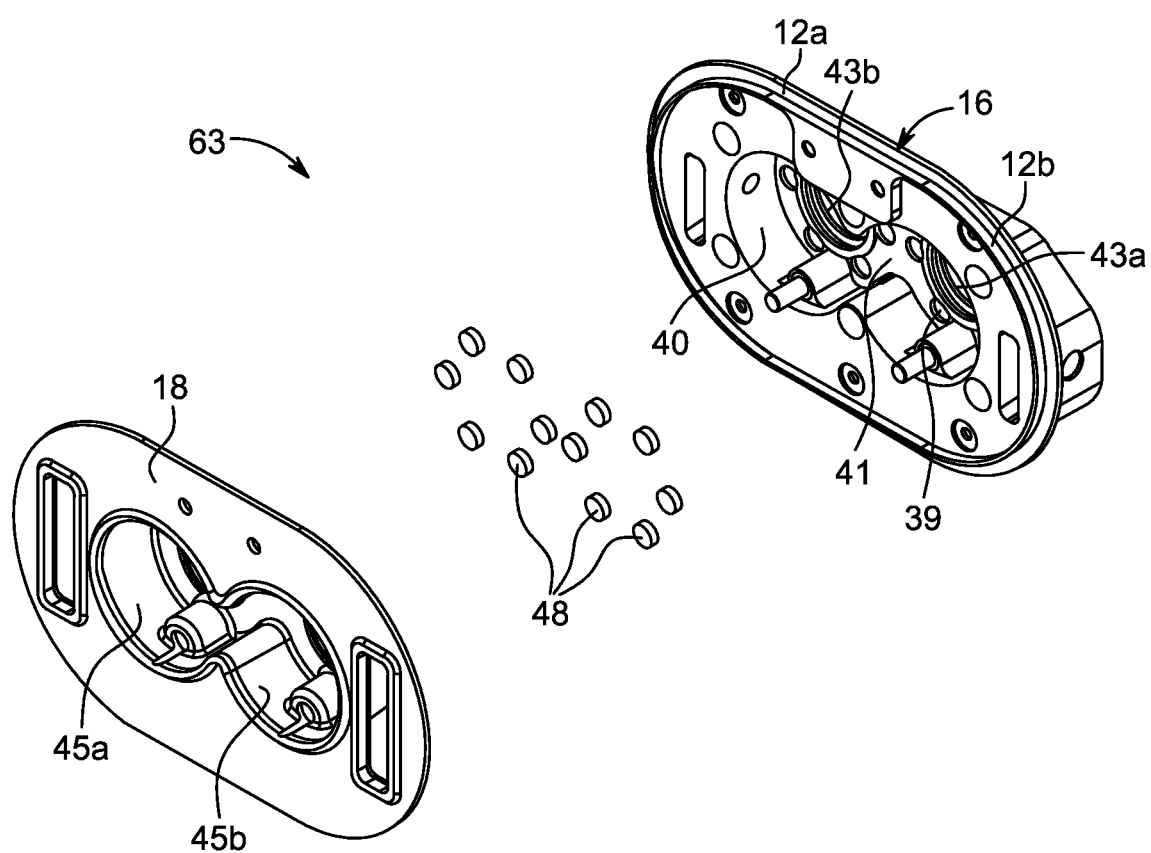
FIG. 5 is an exploded view of a pair of recesses for receiving a pressure jacket.
Figure 6:
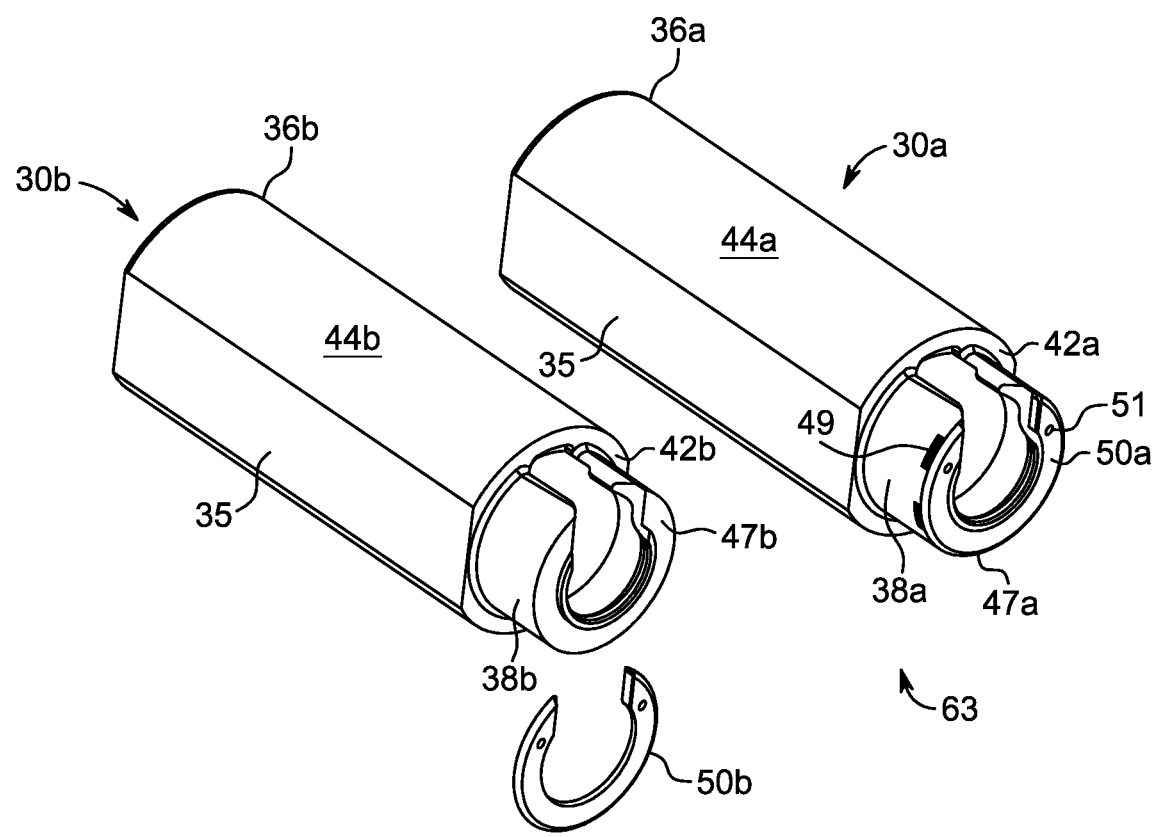
FIG. 6 is an exploded perspective view of the pressure jacket in accordance with certain embodiments.

With reference to FIGS. 5-6, an embodiment of a connection mechanism 63 for coupling the at least one pressure jacket 30a, 30b to the at least one injector heads 12a, 12b is described. In some embodiments, the connection mechanism 63 includes one or more first magnets 48 on the injector head 12a, 12b. The one or more first magnets 48 may be provided on the front end 16 and/or the faceplate 18 of the injector 10 (shown in FIG. 1). In another embodiment, the one or more first magnets 48 may be provided on the proximal end 38a, 38b of the at least one pressure jacket 30a, 30b. In some embodiments, the one or more first magnets 48 may be any permanent or non-permanent magnet. In other embodiments, the one or more first magnets 48 may be one or more electromagnets whose magnetic activation is controlled by a controller. According to certain embodiments, the one or more first magnets 48 may interact with a ferromagnetic material, such as a ferromagnetic metal, on the front end 16, the faceplate 18 of the injector 10 (shown in FIG. 1), or the proximal end 38a, 38b of the at least one pressure jacket 30a, 30b, depending on the location of the one or more first magnets 48. According to these embodiments, the one or more first magnets 48 are configured for being magnetically attracted to the ferromagnetic material. In other embodiments, the one or more first magnets 48, for example on the front end 16 of the injector 10 or the proximal end 38a, 38b of the at least one pressure jacket 30a, 30b may be configured to interact with one or more second magnets (not shown) located of the proximal end 38a, 38b of the at least one pressure jacket 30a, 30b or the front end 16 of the injector 10, respectively. In the embodiment shown in FIG. 5, an exploded view of one embodiment of the front end 16 of the injector head 12a, 12b is shown. The faceplate 18 is provided over the front end 16 such that the faceplate 18 substantially corresponds to the shape of the front end 16 and a recess 40 formed on the front end 16. The faceplate 18 may have at least one recess 45a, 45b that corresponds to the recess 40 on the front end 16. The at least one recess 45a, 45b is configured for receiving at least a portion of the at least one pressure jackets 30a, 30b. The one or more first magnets 48 may be provided on the front end 16 such that the one or more first magnets 48 are positioned along at least a portion of the bottom surface 41 of the recess 40. In some embodiments, the one or more first magnets 48 are recessed relative to the bottom surface 41 of the recess 40. The one or more first magnets 48 may be recessed within one or more magnet pockets 39 such that a top portion of the one or more first magnets 48 is at a same level with the bottom surface 41 of the recess 40. In other embodiments, the one or more first magnets 48 may be provided directly on top of the bottom surface 41. In such embodiments, the one or more first magnets 48 may be recessed within a magnet pocket (not shown) formed on at least a portion of the faceplate 18. In certain embodiments, the one or more first magnets 48 may be located with the magnet pocket on the bottom surface 41 or faceplate 18 and covered by a material, such as a plastic material of the bottom surface 41 or faceplate 18. In one embodiment, a plurality of first magnets 48 are provided around a central opening 43a, 43b through which the drive means 19a, 19b (shown in FIG. 7) extends, such as in a circumferential arrangement. The one or more first magnets 48 may be positioned in close proximity to the faceplate 18 such that the magnetic field from one or more first magnets 48 can permeate through the material of the faceplate 18. The faceplate 18 may be made from a ferromagnetic or non-ferromagnetic material. In other embodiments, one or more first magnets 48 may be provided directly on the faceplate 18. For example, one or more first magnets 48 may be embedded directly into the faceplate 18, or retained on an upper or lower surface of the faceplate 18.

With reference to FIG. 6, the proximal ends 38a, 38b of the pressure jackets 30a, 30b include a ring 50a, 50b that extends around at least a portion of the circumference of the proximal ends 38a, 38b. The ring 50a, 50b may be unitary or formed from a plurality of separate ring segments. The ring 50a, 50b may be retained on at least a portion of a terminal surface 47a, 47b of the pressure jackets 30a, 30b. Because the pressure jackets 30a, 30b are typically constructed from a non-magnetic material, the rings 50a, 50b are desirably made from a ferromagnetic material, although in certain embodiments, the pressure jackets 30a, 30b may be made of a ferromagnetic material, thus obviating the need for ferromagnetic rings 50a, 50b. In one embodiment, the rings 50a, 50b may be made from a magnetic stainless steel material. The rings 50a, 50b are coupled to the rear ends 38a, 38b of the pressure jackets 30a, 30b, for example, by one or more fasteners 51, an interference fit connection, an adhesive connection, and/or by co-molding. The rings 50a, 50b are configured for interacting with the one or more first magnets 48 provided on the front end 16 of the injector heads 12a, 12b. Desirably, the one or more first magnets 48 are arranged in a configuration that substantially corresponds to the shape of the rings 50a, 50b. In some embodiments, when the at least one pressure jacket 30a, 30b is inserted into the recess 45a, 45b on the faceplate 18, at least a portion of the rings 50a, 50b is positioned over the one or more first magnets 48 such that at least one of the one or more first magnets 48 magnetically attracts at least one of the rings 50a, 50b. While FIGS. 5-8 illustrate an embodiment where the first magnets 48 are provided on the front end 16 of the injector heads 12a, 12b, this arrangement can be reversed such that the one or more first magnets 48 are provided on the pressure jackets 30a, 30b. In this arrangement, the first magnets 48 would interact with a ferromagnetic material on the faceplate 18 or the front end 16. In certain embodiments where two pressure jackets 30a, 30b are provided, the orientation of the magnets/ferromagnetic material on individual pressure jackets 30a, 30b and in the individual recesses 45a, 45b on the faceplate 18 may be opposite, such that the individual pressure jackets are specific for a particular recess, such that magnetic attraction between both pressure jackets and the recesses require combination of a specific pressure jacket and a specific recess. This may be desired, for example, when two medical fluids are being delivered (one from each syringe) and require specific pressure jackets for specific medical fluids, such as specific jacket size to accommodate specific syringe size or jacket strength to accommodate specific pressure.

In other embodiments, one or more magnets may be provided on the front end 16 or the faceplate 18 of the injector 10 (shown in FIG. 1) and the proximal end 38a, 38b of the at least one pressure jacket 30a, 30b. With continued reference to FIG. 6, one or more second magnets 49 may be provided on the proximal end 38a, 38b of the at least one pressure jacket 30a, 30b, while the front end 16 or the faceplate 18 of the injector 10 has one or more first magnets 48 as described with reference to FIG. 5. The one or more second magnets 49 may be embedded within the sidewall of the at least one pressure jacket 30a, 30b at the proximal end 38a, 38b. In other embodiments, the one or more second magnets 49 may be retained on at least a portion of the terminal surface 47a, 47b of the pressure jackets 30a, 30b. The poles on one or more first magnets 48 on the front end 16 or the faceplate 18 of the injector 10 may be arranged opposite to the poles on one or more second magnets 49 on the pressure jackets 30a, 30b such that an attractive magnetic force is created when one or more second magnets 49 on the pressure jackets 30a, 30b are brought within the magnetic field of the one or more first magnets 48 on the front end 16 or the faceplate 18 of the injector 10. In some embodiments, the one or more second magnets 49 may be any permanent or non-permanent magnets. In other embodiments, the one or more second magnets 49 may be electromagnets whose magnetic activation is controlled by a controller. In certain embodiments including two pressure jackets, the polar arrangement of the second magnets 49 in one of the pressure jackets may be opposite the polar arrangement of the second magnets 49 in the other pressure jacket; and the polar arrangement of the one or more first magnets 48 in one of the recesses may be opposite the polar arrangement of the one or more first magnets 48 in the other recess. According to this embodiment, a specific pressure jacket will display magnetic attraction with only one of the two recesses and will display magnetic repulsion with the other of the two recesses. This may be desired, for example, when two medical fluids are being delivered (one from each syringe) and require specific pressure jackets for specific medical fluids, as discussed herein.

With reference to FIG. 7, according to an embodiment a pair of pressure jackets 30a, 30b is shown in an assembled configuration with the holding bracket 32 positioned in a first, closed orientation. The distal end 36a, 36b of the pressure jackets 30a, 30b is arranged proximate to the holding bracket 32, while the proximal end 38a, 38b is arranged proximate to the front end 16 of the injector 10. In particular, the undercut portion 42a, 42b of each pressure jacket 30a, 30b is received within at least a portion of the recesses 45a, 45b on the faceplate 18. With reference to the embodiment shown in FIG. 8, which is an enlarged view of Detail A shown in FIG. 7, the ring 50b of pressure jacket 30b is positioned opposite the one or more first magnets 48 such that the magnetic field of the one or more first magnet 48 interacts with the ferromagnetic material of the ring 50b. In this manner, the magnetic force of the one or more first magnets 48 draws the ring 50b axially toward the one or more first magnet 48 such that the ring 50b, along with the pressure jacket 30b, is retained on the injector head 12b. Pressure jacket 30a may be retained in a similar manner. In order to disconnect the pressure jackets 30a, 30b from the injector heads 12a, 12b, such as during cleaning or maintenance, the pressure jackets 30a, 30b are urged away from the one or more first magnets 48 in an axial direction from the proximal end to the distal end of the pressure jackets 30a, 30b with a sufficient axially directed force to overcome the attractive force of the one or more first magnets 48 that hold the pressure jackets 30a, 30b against the injector heads 12a, 12b. Alternatively, in embodiments where the one or more first magnets 48 comprises an electromagnet, the electric current to the one or more first magnets 48 may be shut off, thereby eliminating the electromagnetic attractive force and allowing disconnection of the one or more pressure jacket 30a, 30b. Each pressure jacket 30a, 30b may be disconnected by pulling the pressure jacket 30a, 30b manually or by a manual or automated mechanism that disconnects the pressure jacket 30a, 30b from the injector head 12a, 12b.

During an injection procedure, axial movement of the at least one pressure jackets 30a, 30b may cause the pressure jackets to be disconnected from the injector heads 12a, 12b if the axial force exceeds the magnetic force of the first magnets 48, although the pressure jacket is generally retained in the engaged position by holding bracket 32. Such movement reduces the stress that would normally be present at the interface between the pressure jackets 30a, 30b and the injector heads 12a, 12b if the pressure jackets 30a, 30b were rigidly connected to the injector heads 12a, 12b. Further distal movement of the pressure jackets 30a, 30b is restricted by the holding bracket 32. Upon completion of the injection procedure, the pressure jackets 30a, 30b are reconnected to the injector heads 12a, 12b under the action of the magnetic force of the one or more first magnets 48.

Figure 10:
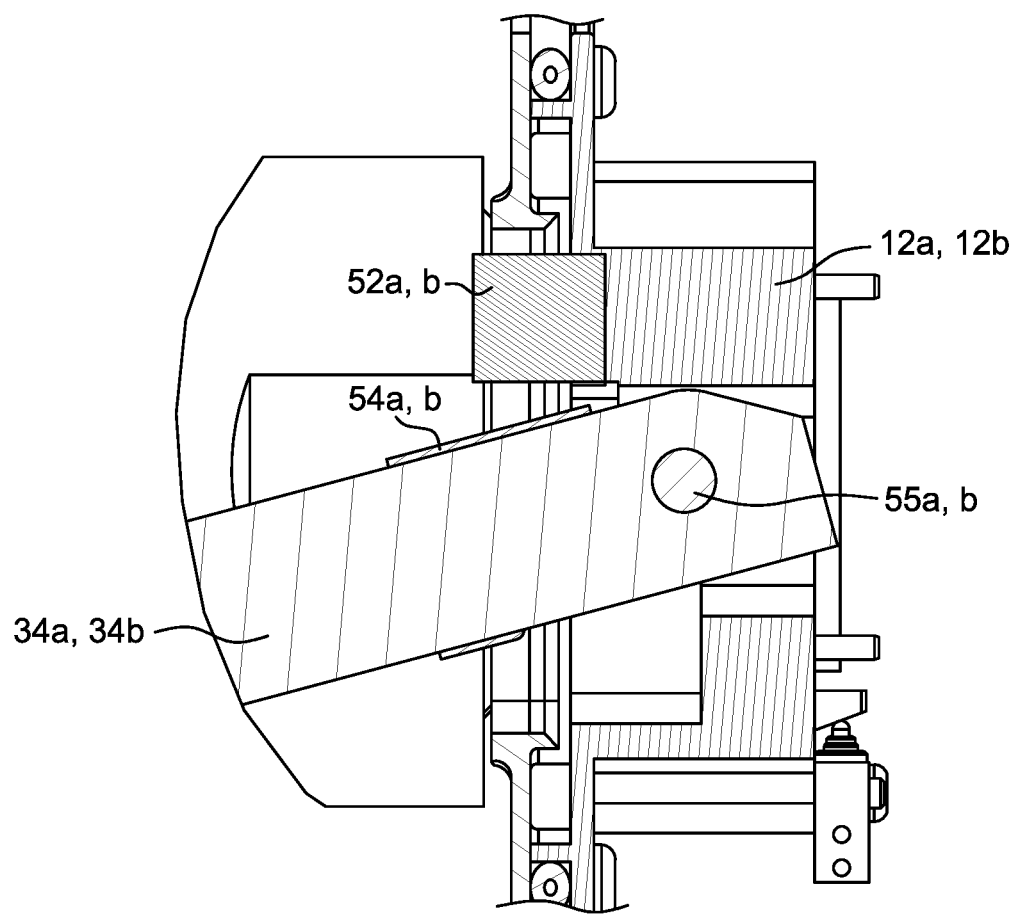
FIG. 10 is an enlarged view of Detail B shown in FIG. 9.

With reference to FIGS. 9-10, an embodiment of a retention mechanism 51a, 51b for retaining the arms 34a, 34b in a second, open position is illustrated. Referring initially to FIG. 9, the arms 34a, 34b (only arm 34b is illustrated) are pivotable around the pivot point 55a, 55b on the injector 10. As described above with reference to FIGS. 2-3, the arms 34a, 34b are movable between a first, closed position (FIG. 2) and a second, open position (FIGS. 3 and 9) by pivoting about the pivot point 55a, 55b. In certain embodiments where the holding bracket 32 is substantially heavier than the arms 34a, 34b, a significant torque may be exerted at the pivot point 55a, 55b, which tends to urge the arms 34a, 34b in a downward direction. In order to prevent the arms 34a, 34b from being pulled downward due to this torque, the retention mechanism 51a, 51b may be provided that includes at least one third magnet 52a, 52b on the injector 10 that interacts with the at least one ferromagnetic element 54a, 54b provided on the arms 34a, 34b to retain the arms 34a, 34b in a closed position. With reference to FIG. 10, which is an enlarged view of Detail B in FIG. 9, the third magnet 52a, 52b may be provided on the injector heads 12a, 12b and the ferromagnetic element 54a, 54b may be provided on the arms 34a, 34b. In one embodiment, the ferromagnetic element 54a, 54b is affixed to the arms 34a, 34b. In some embodiments, the third magnet 52a, 52b may be provided on only one of the injector heads 12a, 12b and the ferromagnetic element 54a, 54b may be provided on the corresponding arm 34a or 34b. In other embodiments, the third magnet 52a, 52b may be provided on the arms 34a, 34b, while the ferromagnetic element 54a, 54b is provided on the injector heads 12a, 12b. In other embodiments, two third magnets 52a, 52b having opposite poles may be provided on the arms 34a, 34b and the injector heads 12a, 12b. In some embodiments, the third magnet 52a, 52b may be any permanent or non-permanent magnet. In other embodiments, the third magnet 52a, 52b may be an electromagnet whose magnetic activation is controlled by a controller.

In an open position (FIG. 10), the ferromagnetic element 54a, 54b is not magnetically retained by the third magnet 52a, 52b, thereby allowing the arms 34a, 34b to swing downward. As the arms 34a, 34b are pivoted to a closed position (FIG. 11) by swinging the arms 34a, 34b in an upward direction, the magnetic force of the third magnet 52a, 52b attracts the ferromagnetic element 54a, 54b to retain the arms 34a, 34b in a closed position and prevent them from pivoting downward away from the closed position. In some embodiments, one or more third magnets 52a, 52b may be monolithically formed with one or more first magnets 48 on the front end 16 or the faceplate 18 such that a single magnet on each recess 45a, 45b is configured for retaining each of the corresponding at least one of the pressure jackets 30a, 30b and the corresponding at least one of the arms 34a, 34b.

Figure 11:
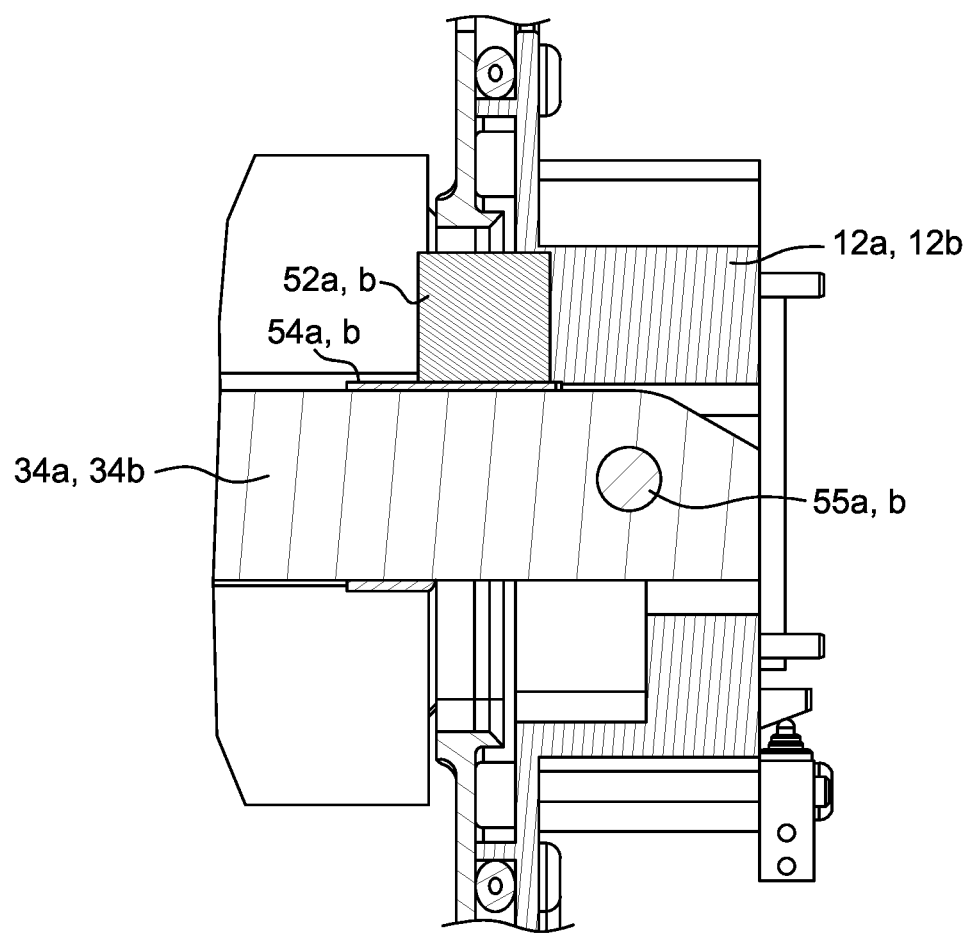
FIG. 11 is an enlarged view of Detail B in FIG. 9 showing the fluid injector in a first, closed position.

While FIGS. 9-11 illustrate an embodiment where the third magnet 52a, 52b is provided on the at least one of the injector heads 12a, 12b and the ferromagnetic element 54a, 54b is provided on the at least one of the arms 34a, 34b, this arrangement may be reversed such that the ferromagnetic element 54a, 54b is provided on the injector heads 12a, 12b and the third magnet 52a, 52b is provided on the arms 34a, 34b. Additionally, in an embodiment where the arms 34a, 34b are made from ferromagnetic material, the ferromagnetic element 54a, 54b may be a portion of the arms 34a, 34b. Similarly, in an embodiment where the ferromagnetic element 54a, 54b is provided on the injector heads 12a, 12b, the ferromagnetic element 54a, 54b may be a ferromagnetic portion of the injector heads 12a, 12b. In other embodiments, at least one of the arms 34a, 34b may have a magnet and the at least one of the injector heads 12a, 12b may have a magnet having an opposite magnetic pole facing the at least one of the arms 34a, 34b when the arms 34a, 34b are in the closed position.

With reference to FIG. 9, the holding bracket 32 is pivotable about the second pivot point 57a, 57b at the distal end 59a, 59b of the arms 34a, 34b in a direction of arrow B. In some embodiments, pivoting movement of the holding bracket 32 provides additional room for installation of the at least one pressure jacket 30a, 30b and/or the at least one syringe 22a, 22b onto the injector 10. In various embodiments, one or more fourth magnets 60a, 60b may be provided on the holding bracket 32 to magnetically interact with at least a portion of the at least one of the arms 34a, 34b or a ferromagnetic portion at the distal end 59a, 59b thereof. The one or more fourth magnets 60a, 60b may be configured to retain the holding bracket 32 in a substantially perpendicular orientation relative to a longitudinal length of the arms 34a, 34b. The one or more fourth magnets 60a, 60b may be configured to magnetically interact with at least a portion of the arms 34a, 34b to retain the holding bracket 32 when the arms 34a, 34b are within the magnetic field of the one or more fourth magnets 60a, 60b. While FIG. 9 illustrates an embodiment where the one or more fourth magnets 60a, 60b are provided on the holding bracket 32, this arrangement may be reversed such that the one or more fourth magnets 60a, 60b are provided on the arms 34a, 34b. In other embodiments, the at least one of the arms 34a, 34b may have a fourth magnet and the holding bracket 32 may have a fifth magnet having an opposite magnetic pole facing the at least one of the arms 34a, 34b. In other embodiments, the one or more fourth magnets may interact with a ferromagnetic element on the distal end 36a, 36b of the at least one pressure jackets 30a, 30b to retain the holding bracket 32 against the at least one pressure jacket 30a, 30b. As before, this arrangement may be reversed, or may include magnets with opposite polar arrangements on the holding bracket 32 and the distal end 36a, 36b of the at least one pressure jackets 30a, 30b.

While various embodiments of the fluid delivery system with a magnetically-retain pressure jacket were provided in the foregoing description, those skilled in the art may make modifications and alterations to these embodiments without departing from the scope and spirit of the disclosure. For example, it is to be understood that this disclosure contemplates that, to the extent possible, one or more features of any embodiment can be combined with one or more features of any other embodiment. Accordingly, the foregoing description is intended to be illustrative rather than restrictive.

We claim:

1. A fluid injector comprising:
  at least one injector head having a front end configured to releasably receive at least one syringe;
  at least one pressure jacket releasably associated with the front end of the at least one injector head for securing the at least one syringe during an injection procedure; and
  a connection mechanism for releasably connecting the at least one pressure jacket to the front end of the at least one injector head,
  wherein the connection mechanism comprises at least one electromagnet,
  wherein an electromagnetic force of the at least one electromagnet is controlled by a controller of the fluid injector.

2. The fluid injector of claim 1, wherein the at least one injector head comprises the at least one electromagnet.

3. The fluid injector of claim 2, wherein the at least one electromagnet is configured to magnetically interact with at least one magnet associated with the at least one pressure jacket.

4. The fluid injector of claim 3, wherein poles of the at least one electromagnet on the front end of the at least one injector head is opposite to poles of the at least one magnet associated with the at least one pressure jacket.

5. The fluid injector of claim 3, wherein the at least one magnet associated with the at least one pressure jacket comprises a ferromagnetic material.

6. The fluid injector of claim 1, wherein the at least one injector head is configured to releasably receive two syringes.

7. The fluid injector of claim 6, wherein the fluid injector comprises two pressure jackets.

8. The fluid injector of claim 7, wherein the two pressure jackets comprise a first pressure jacket and a second pressure jacket, wherein a polar arrangement of at least one magnet in the first pressure jacket is opposite the polar arrangement of the at least one magnet in the second pressure jacket, and
  wherein the at least one injector head comprises a face plate comprising a first recess and a second recess configured for retaining a first pressure jacket and a second pressure jacket, respectively,
  wherein an electromagnet in the first recess are opposite the polarity of an electromagnet in the second recess, such that the at least on magnet of the first pressure jacket is magnetically attracted to the electromagnet of the first recess and not the electromagnet of the second recess, and
  the at least on magnet of the second pressure jacket is magnetically attracted to the electromagnet of the second recess and not the electromagnet of the first recess.

9. The fluid injector of claim 1, further comprising at least one arm pivotally connected at a proximal end to the at least one injector head for retaining a distal end of the at least one pressure jacket, wherein the at least one arm is pivotable between a first position and a second position.

10. The fluid injector of claim 9, wherein the at least one arm is magnetically retained in the first position.

11. The fluid injector of claim 9, further comprising a holding bracket pivotally connected to a distal end of the at least one arm for engaging the distal end of the at least one pressure jacket, wherein the holding bracket is pivotable between a first holding bracket position and a second holding bracket position.

12. The fluid injector of claim 9, wherein the holding bracket is magnetically retained in the first holding bracket position.

13. The fluid injector of claim 11, wherein the at least one pressure jacket is configured to move axially against a magnetic attractive force between the at least one pressure jacket and the fluid injector while the pressure jacket is still in an engaged position with the fluid injector by the holding bracket.

14. The fluid injector of claim 1, wherein a controller of the fluid injector is configured to disconnect the electric current to the at least one electromagnet to eliminate an electromagnetic attractive force between the front end of the fluid injector and a proximal end of the at least one pressure jacket to allow disconnection of the at least one pressure jacket from the fluid injector.

15. A pressure jacket for use with a fluid injector, the pressure jacket comprising:
- a tubular body having a proximal end and a distal end;
- a syringe receiving opening at the proximal end or the distal end configured for receiving a syringe within an interior of the tubular body;
- a connection portion with a terminal surface at the proximal end configured for releasably connecting the pressure jacket to the fluid injector; and
- at least one magnetic element on at least a portion of the connection portion configured to magnetically interact with an electromagnet on a front end of a head of the fluid injector for releasably connecting the pressure jacket to the fluid injector,
- wherein the pressure jacket is made of a ferromagnetic material.

* * * * *

UNITED STATES PATENT AND TRADEMARK OFFICE
CERTIFICATE OF CORRECTION

PATENT NO. : 10,888,651 B2  
APPLICATION NO. : 16/160389  
DATED : January 12, 2021  
INVENTOR(S) : Dedig et al.

Page 1 of 1

It is certified that error appears in the above-identified patent and that said Letters Patent is hereby corrected as shown below:

In the Specification  
In Column 1, Line 8, delete "2016," and insert -- 2016, now Pat. No. 10,124,110, --, therefor.  
In Column 6, Lines 47-48, delete "end 26a, 26b" and insert -- end 25a, 25b --, therefor.

In the Claims  
In Column 12, Line 53, in Claim 8, delete "the" and insert -- a --, therefor. (second occurrence)  
In Column 12, Line 54, in Claim 8, delete "of the at" and insert -- of at --, therefor.  
In Column 12, Line 57, in Claim 8, delete "a" and insert -- the --, therefor. (first occurrence)  
In Column 12, Line 57, in Claim 8, delete "a" and insert -- the --, therefor. (second occurrence)  
In Column 12, Line 59, in Claim 8, delete "are" and insert -- is --, therefor.  
In Column 12, Line 61, in Claim 8, delete "on" and insert -- one --, therefor.  
In Column 12, Line 65, in Claim 8, delete "on" and insert -- one --, therefor.  
In Column 13, Line 22, in Claim 14, delete "a" and insert -- the --, therefor.  
In Column 13, Line 23, in Claim 14, delete "the" and insert -- an --, therefor.

Signed and Sealed this  
Sixteenth Day of March, 2021

Drew Hirshfeld  
*Performing the Functions and Duties of the*  
*Under Secretary of Commerce for Intellectual Property and*  
*Director of the United States Patent and Trademark Office*